(12) United States Patent
Sugiyama et al.

(10) Patent No.: US 7,508,516 B2
(45) Date of Patent: Mar. 24, 2009

(54) BIOCHIP READING APPARATUS AND BIOCHIP READING METHOD

(75) Inventors: Yumiko Sugiyama, Tokyo (JP); Takeo Tanaami, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 11/527,565

(22) Filed: Sep. 27, 2006

(65) Prior Publication Data

US 2007/0070350 A1    Mar. 29, 2007

(30) Foreign Application Priority Data

Sep. 27, 2005    (JP)    ............ P. 2005-279507

(51) Int. Cl.
  *G01N 21/64*    (2006.01)
  *G01N 21/55*    (2006.01)
(52) U.S. Cl. .............. 356/417; 356/318; 356/432; 356/445; 250/458.1; 436/172
(58) Field of Classification Search ........... 356/317, 356/318, 417, 401
  See application file for complete search history.

(56) References Cited

U.S. PATENT DOCUMENTS 6,537,801 B1 *    3/2003    Ida et al. ............. 435/287.2

2003/0170672 A1    9/2003    Cho et al.
2004/0224318 A1    11/2004    Mahant et al.

FOREIGN PATENT DOCUMENTS

| EP | 1-347-285 A1 | 9/2003 |
|---|---|---|
| GB | 2-355-716 A | 5/2001 |
| JP | 2000-292353 A | 10/2000 |
| WO | WO 03/100474 A2 * | 12/2003 |

OTHER PUBLICATIONS

Optics, Optical Technology in Life Science "DNA Analysis and Optical Technology", vol. 28, No. 10(1999), (Aggregate Corporation) Society Committee of Applied Physics, Japan Optical Society, 1999, p. 549-552.

* cited by examiner

*Primary Examiner*—F. L. Evans
(74) *Attorney, Agent, or Firm*—Sughrue Mion, PLLC

(57) ABSTRACT

A site position can be detected using transmitted light or reflected light which does not include an excitation wavelength according to a configuration of a biochip 60. When reflected light is used, a light source 21 is actuated. Light from the light source 21 passes through a barrier filter 22 and is bent by a dichroic mirror 23 and passes through a dichroic mirror 3 and illuminates the biochip 60. The reflected light in the biochip 60 enters a CCD camera 13. An output signal of the CCD camera 13 is sent to a computation part 51 and a position of a site on the biochip 60 is detected in the computation part 51.

28 Claims, 3 Drawing Sheets

BIOCHIP READING APPARATUS AND BIOCHIP READING METHOD

BACKGROUND OF THE INVENTION

The present invention relates to a biochip reading apparatus and a biochip reading method for making an analysis based on distribution of the light quantity of fluorescence generated at a site on a biochip.

A method using a biochip is known as a method for identifying a biopolymer such as DNA. For example, in the case of identifying DNA, a DNA probe having the known base sequence is fixed to each of the sites of a biochip and DNA having the complementary base sequence is bound to each of the sites by hybridization. The amount of binding can be recognized as the light quantity of fluorescence by labeling the bound DNA with a fluorescent molecule.

[Non-Patent Reference 1]

Touru Makino, Kyouichi Kano, Journal "Optics", Optical Technology in Life Science "DNA Analysis and Optical Technology", Volume 28, No. 10 (1999), (Aggregate Corporation) Society Committee of Applied Physics, Japan Optical Society, 1999, p. 549-552

The light quantity is measured using a dedicated reading apparatus. It is necessary to detect a position of a site in order to measure the light quantity of each of the sites. A method for detecting a position of a site includes a method for being irradiated with excitation light and using fluorescence of each of the sites and a method for illuminating a biochip by white illumination and checking a position of a site.

However, in the former method, it is difficult to detect a site with dark fluorescence and also brightness of a site varies depending on the number of fluorescent molecules, so that the light quantity varies every site and an accurate position cannot be detected. Also, there is a problem that color fading occurs in fluorescence by being irradiated with excitation light.

Also, in the latter method, a wavelength of excitation light is included in white light, so that fluorescent molecules of a site are excited and color fading of fluorescence is inevitable. Also, the fluorescent molecules of each of the sites are excited, so that brightness of each of the sites varies depending on the number of fluorescent molecules and it is difficult to detect an accurate position.

SUMMARY OF THE INVENTION

An object of the invention is to provide a biochip reading apparatus and a biochip reading method capable of accurately detecting a position of a site on a biochip.

A biochip reading apparatus of the invention is characterized in that in a biochip reading apparatus for making an analysis based on distribution of the light quantity of fluorescence generated at a site on a biochip, the apparatus comprises illumination member for irradiating a biochip with illumination light which does not include an excitation wavelength, and detection member for detecting a position of a site on a biochip based on reflected light or transmitted light of the illumination light.

According to this biochip reading apparatus, a biochip is irradiated with illumination light which does not include an excitation wavelength and a position of a site on the biochip is detected based on transmitted light or reflected light of the illumination light, so that the site can be illuminated by uniform brightness without causing color fading of fluorescence and the position of the site can be accurately detected.

A biochip reading apparatus of the invention is characterized in that in a biochip reading apparatus for making an analysis based on distribution of the light quantity of fluorescence generated at a site on a biochip, the apparatus comprises illumination member for irradiating a biochip with illumination light of a wavelength longer than an excitation wavelength, and detection member for detecting a position of a site on a biochip based on reflected light or transmitted light of the illumination light. According to this biochip reading apparatus, a biochip is irradiated with illumination light of a wavelength longer than an excitation wavelength and a position of a site on the biochip is detected based on transmitted light or reflected light of the illumination light, so that the site can be illuminated by uniform brightness without causing color fading of fluorescence and the position of the site can be accurately detected.

The illumination member may be equipped with a light source and a filter for limiting a wavelength of light applied from the light source.

The illumination member may be constructed of a light emitting diode.

The illumination member may be constructed of electroluminescence.

A biochip reading method of the invention is characterized in that in a biochip reading method for making an analysis based on distribution of the light quantity of fluorescence generated at a site on a biochip, the method comprises the steps of irradiating a biochip with illumination light which does not include an excitation wavelength, and detecting a position of a site on a biochip based on reflected light or transmitted light of the illumination light.

According to this biochip reading method, a biochip is irradiated with illumination light which does not include an excitation wavelength and a position of a site on the biochip is detected based on transmitted light or reflected light of the illumination light, so that the site can be illuminated by uniform brightness without causing color fading of fluorescence and the position of the site can be accurately detected.

A biochip reading method of the invention is characterized in that in a biochip reading method for making an analysis based on distribution of the light quantity of fluorescence generated at a site on a biochip, the method comprises the steps of irradiating a biochip with illumination light of a wavelength longer than an excitation wavelength, and detecting a position of a site on a biochip based on reflected light or transmitted light of the illumination light. According to this biochip reading method, a biochip is irradiated with illumination light of a wavelength longer than an excitation wavelength and a position of a site on the biochip is detected based on transmitted light or reflected light of the illumination light, so that the site can be illuminated by uniform brightness without causing color fading of fluorescence and the position of the site can be accurately detected.

A light source and a filter for limiting a wavelength of light applied from the light source may be used in the illuminating step.

A light emitting diode may be used in the illuminating step.

Electroluminescence may be used in the illuminating step.

According to a biochip reading apparatus of the invention, a biochip is irradiated with illumination light which does not include an excitation wavelength and a position of a site on the biochip is detected based on transmitted light or reflected light of the illumination light, so that the site can be illuminated by uniform brightness without causing color fading of fluorescence and the position of the site can be accurately detected.

According to a biochip reading apparatus of the invention, a biochip is irradiated with illumination light of a wavelength longer than an excitation wavelength and a position of a site on the biochip is detected based on transmitted light or reflected light of the illumination light, so that the site can be illuminated by uniform brightness without causing color fading of fluorescence and the position of the site can be accurately detected.

According to a biochip reading method of the invention, a biochip is irradiated with illumination light which does not include an excitation wavelength and a position of a site on the biochip is detected based on transmitted light or reflected light of the illumination light, so that the site can be illuminated by uniform brightness without causing color fading of fluorescence and the position of the site can be accurately detected.

According to a biochip reading method of the invention, a biochip is irradiated with illumination light of a wavelength longer than an excitation wavelength and a position of a site on the biochip is detected based on transmitted light or reflected light of the illumination light, so that the site can be illuminated by uniform brightness without causing color fading of fluorescence and the position of the site can be accurately detected.

BRIEF DESCRIPTION OF THE DRAWINGS

FIG. 3A is a perspective diagram, and FIG. 3B is a sectional diagram taken on line B-B of FIG. 3A.

DETAILED DESCRIPTION OF THE PREFERRED EMBODIMENTS

One embodiment of a biochip reading apparatus according to the invention will be described below with reference to FIGS. 1 to 3.

Figure 1:
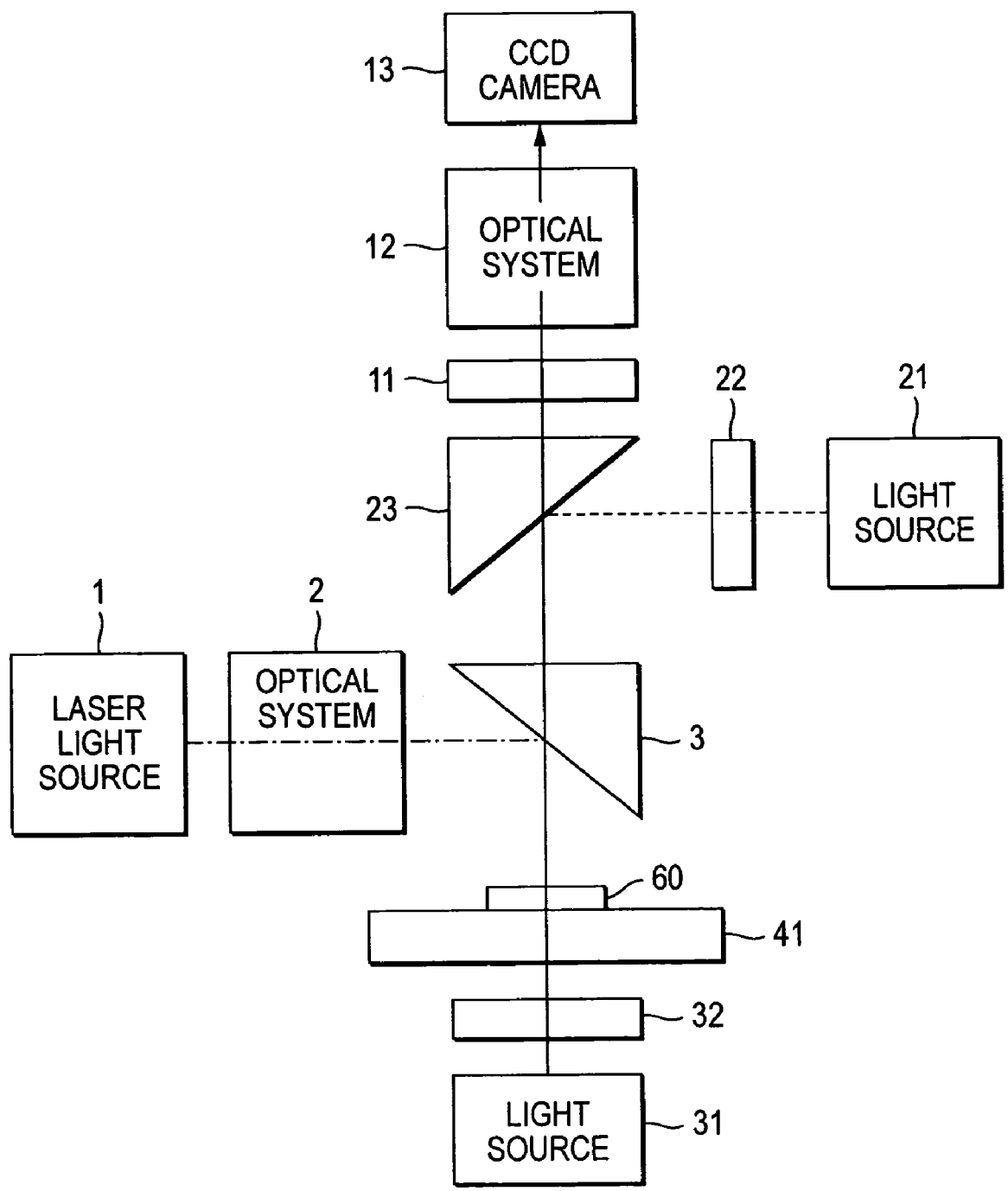
FIG. 1 is a diagram showing a configuration of an optical system of a biochip reading apparatus of the present embodiment.

FIG. 1 is a diagram showing a configuration of an optical system of a biochip reading apparatus of the present embodiment.

As shown in FIG. 1, the biochip reading apparatus of the embodiment comprises a laser light source 1 for generating excitation light, an optical system 2 and a dichroic mirror 3 for bending laser light as an optical system for irradiating a biochip 60 with excitation light.

A wavelength of the laser light source 1 matches with excitation light of a fluorescent molecule of, for example, cy3 or cy5.

Also, the biochip reading apparatus of the embodiment comprises a barrier filter 11 arranged in an optical path, an optical system 12 and a CCD camera 13 for receiving light passing through the optical system 12 as an optical system for receiving light from the biochip 60.

Further, the biochip reading apparatus of the embodiment comprises alight source 21 for outputting white light, a barrier filter 22 and a dichroic mirror 23 for bending light from the light source 21 as an optical system for performing reflected illumination of the biochip 60. The barrier filter 22 has a function of transmitting only the light of a wavelength longer than that of excitation light or removing a wavelength component of excitation light of a fluorescent molecule among the light outputted from the light source 21.

Furthermore, the biochip reading apparatus of the embodiment comprises a light source 31 for outputting white light and a barrier filter 32 as an optical system for performing transmitted illumination of the biochip 60. The barrier filter 32 has a function of transmitting only the light of a wavelength longer than that of excitation light or removing a wavelength component of excitation light of a fluorescent molecule among the light outputted from the light source 31.

The biochip 60 is placed on a table 41 as shown in FIG. 1.

Figure 2:
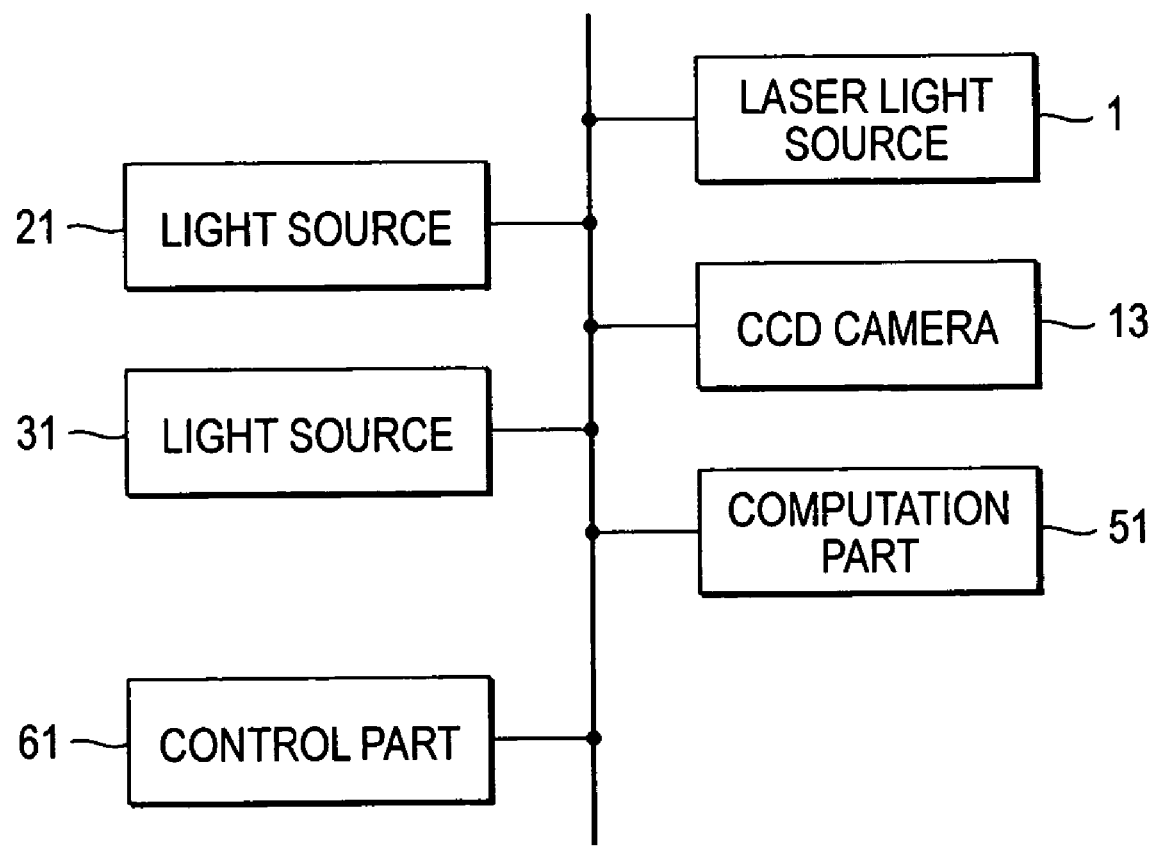
FIG. 2 is a block diagram showing a configuration of a control system of the biochip reading apparatus of the embodiment.

FIG. 2 is a block diagram showing a configuration of a control system of the biochip reading apparatus of the embodiment.

As shown in FIG. 2, the biochip reading apparatus of the embodiment comprises a computation part 51 for performing various computations, a laser light source 1, a light source 21, a light source 31, a CCD camera 13 and a control part 61 for controlling the computation part 51.

Next, a procedure for detecting a position of a site on the biochip 60 will be described.

In the embodiment, a site position can be detected using reflected light or transmitted light according to a configuration of a biochip.

When reflected light is used, the light source 21 is actuated. Light from the light source 21 passes through the barrier filter 22 and is bent by the dichroic mirror 23 and passes through the dichroic mirror 3 and illuminates the biochip 60. The reflected light in the biochip 60 travels upward in FIG. 1 and enters the CCD camera 13. An output signal of the CCD camera 13 is sent to the computation part 51 and a position of a site on the biochip 60 is detected in the computation part 51. The position of the site is detected based on, for example, a coordinate system (a position of a corresponding pixel) of the CCD camera 13.

In the embodiment as described above, the barrier filter 22 transmits only the light of a wavelength longer than that of excitation light or removes a wavelength component of excitation light of a fluorescent molecule among the light outputted from the light source 21. Therefore, damage of fluorescence fading is not caused by illumination light with which the biochip 60 is irradiated. Also, a position of a site is detected by illumination light of the biochip 60 without using fluorescence, so that all the sites can be captured by uniform brightness. Therefore, the position of the site can be detected with high accuracy.

When transmitted light is used in detection of a site position, the light source 31 is actuated. Light from the light source 31 passes through the barrier filter 32 and illuminates the biochip 60 from the side of the table 41. In a manner similar to the reflected light, the transmitted light travels upward in FIG. 1 and enters the CCD camera 13. An output signal of the CCD camera 13 is sent to the computation part 51 and a position of a site on the biochip 60 is detected in the computation part 51.

In the embodiment as described above, the barrier filter 32 transmits only the light of a wavelength longer than that of excitation light or removes a wavelength component of excitation light of a fluorescent molecule among the light outputted from the light source 31. Therefore, damage of fluorescence fading is not caused by illumination light with which the biochip 60 is irradiated. Also, a position of a site is detected by illumination light of the biochip 60 without using fluorescence, so that all the sites can be captured by uniform brightness. Therefore, the position of the site can be detected with high accuracy.

Next, an action at the time of measurement of the biochip 60 will be described.

At the time of measurement, laser light outputted from the laser light source 1 passes through the optical system 2 and is bent by the dichroic mirror 3 and the biochip 60 is irradiated with the laser light.

Fluorescence from the biochip 60 generated by excitation by the laser light enters the CCD camera 13 through the dichroic mirror 3, the dichroic mirror 23, the barrier filter 11 and the optical system 12. An output signal of the CCD camera 13 is sent to the computation part 51 and the light quantity of fluorescence of each of the sites on the biochip 60 is measured in the computation part 51.

It is necessary to identify a position of each of the sites in order to calculate the light quantity of fluorescence of each of the sites. Here, according to a result of detection by the procedure described above, a position of the site is clipped from an image by the CCD camera 13 by image processing and then the light quantity of its region is measured. In the embodiment as described above, the position of the site is accurately detected by uniform illumination light without influence of fluorescence, so that the light quantity of each of the sites can be measured with high accuracy.

In addition, a position of a site may be detected after fluorescence from the biochip 60 is captured by a CCD camera. The light quantity of fluorescence can be measured by later clipping a captured image based on a result of detection of the site position.

In the embodiment as described above, illumination methods can be selected properly according to a structure of a biochip. For example, in a through type chip, the outline of a site can be recognized by using transmitted light and a position of the site can be detected. Also, in a chip in which DNA is arranged on glass, when transmittance or reflectance changes at a wavelength measured by particles bound to the DNA or the DNA, the site can be detected similarly. Or, when a site is formed in convex shape, transmission or reflection changes, so that the site can be detected.

Figure 3A:
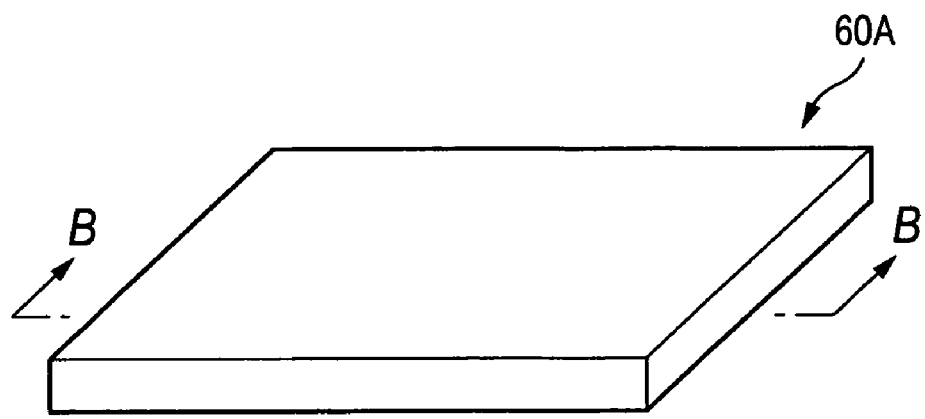
FIGS. 3A and 3B are diagrams showing a structure of a through type chip.
Figure 3B:
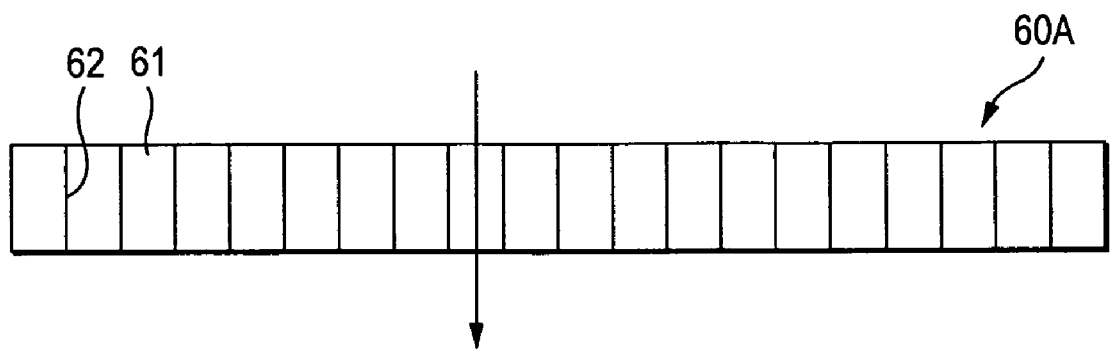

FIG. 3 is a diagram showing a structure of a through type chip 60A, and FIG. 3A is a perspective diagram, and FIG. 3B is a sectional diagram taken on line B-B of FIG. 3A. As shown in FIGS. 3A and 3B, in the through type chip 60A, detection regions 61 in which probes corresponding to individual target molecules are fixed are two-dimensionally arranged in a container formed by resin and each of the detection regions 61 is partitioned by partition walls 62. Each of the detection regions 61 detects the target molecules in a solution extending through a thickness direction (upward and downward directions in FIG. 3B) of the through type chip 60A by hybridization. Since the partition walls 62 are opaque to the transmitted light, positions of the detection regions 61 (sites) can be detected. Also, when the partition walls 62 have reflectance, the positions can be detected by reflected light.

In the embodiment described above, illumination light is obtained by combining a white light source and a barrier filter, but instead of this, an LED, electroluminescence or a laser light source, etc. for outputting light of a predetermined wavelength satisfying a condition of illumination member in the invention can also be used.

The applicable scope of the invention is not limited to the embodiment described above. The invention can be widely applied to a biochip reading apparatus and a biochip reading method for making an analysis based on distribution of the light quantity of fluorescence generated at a site on a biochip.

What is claimed is:

1. A biochip reading apparatus for making an analysis based on distribution of the light quantity of fluorescence generated at a site on a biochip, comprising:
    illumination member for irradiating a biochip with illumination light which does not include an excitation wavelength, and
    detection member for detecting a position of a site on a biochip based on reflected light or transmitted light of the illumination light.

2. A biochip reading apparatus for making an analysis based on distribution of the light quantity of fluorescence generated at a site on a biochip, comprising:
    illumination member for irradiating a biochip with illumination light of a wavelength longer than an excitation wavelength, and
    detection member for detecting a position of a site on a biochip based on reflected light or transmitted light of the illumination light.

3. The biochip reading apparatus as claimed in claim 1, wherein the illumination member is equipped with a light source and a filter for limiting a wavelength of light applied from the light source.

4. The biochip reading apparatus as claimed in claim 1, wherein the illumination member is constructed of a light emitting diode.

5. The biochip reading apparatus as claimed in claim 1, wherein the illumination member is constructed of electroluminescence.

6. A biochip reading method for making an analysis based on distribution of the light quantity of fluorescence generated at a site on a biochip, comprising the steps of:
    irradiating a biochip with illumination light which does not include an excitation wavelength, and
    detecting a position of a site on a biochip based on reflected light or transmitted light of the illumination light.

7. A biochip reading method for making an analysis based on distribution of the light quantity of fluorescence generated at a site on a biochip, comprising the steps of:
    irradiating a biochip with illumination light of a wavelength longer than an excitation wavelength, and
    detecting a position of a site on a biochip based on reflected light or transmitted light of the illumination light.

8. The biochip reading method as claimed in claim 6, wherein a light source and a filter for limiting a wavelength of light applied from the light source are used in the illuminating step.

9. The biochip reading method as claimed in claim 6, wherein a light emitting diode is used in the illuminating step.

10. The biochip reading method as claimed in claim 6, wherein electroluminescence is used in the illuminating step.

11. The biochip reading apparatus as claimed in claim 2, wherein the illumination member is equipped with a light source and a filter for limiting a wavelength of light applied from the light source.

12. The biochip reading apparatus as claimed in claim 2, wherein the illumination member is constructed of a light emitting diode.

13. The biochip reading apparatus as claimed in claim 2, wherein the illumination member is constructed of electroluminescence.

14. The biochip reading method as claimed in claim 7, wherein a light source and a filter for limiting a wavelength of light applied from the light source are used in the illuminating step.

15. The biochip reading method as claimed in claim 7, wherein a light emitting diode is used in the illuminating step.

16. The biochip reading method as claimed in claim 7, wherein electroluminescence is used in the illuminating step.

17. The biochip reading apparatus as claimed in claim 1, wherein a position of the site of the analysis based on the distribution of the light quantity of fluorescence generated at the site on the biochip corresponds to the position of the site on the biochip detected by the detection member based on the reflected light or the transmitted light of the illumination light.

18. The biochip reading apparatus as claimed in claim 1, wherein the transmitted light illuminates the site through the biochip.

19. The biochip reading apparatus as claimed in claim 1, wherein the site on the biochip comprises:
  a biopolymer probe fixed to the site; and
  a DNA probe having the known base sequence fixed to the site.

20. The biochip reading apparatus as claimed in claim 2, wherein a position of the site of the analysis based on the distribution of the light quantity of fluorescence generated at the site on the biochip corresponds to the position of the site on the biochip detected by the detection member based on the reflected light or the transmitted light of the illumination light.

21. The bio chip reading apparatus as claimed in claim 2, wherein the transmitted light which illuminates the site through the biochip.

22. The biochip reading apparatus as claimed in claim 2, wherein the site on the biochip comprises:
  a biopolymer probe fixed to the site; and
  a DNA probe having the known base sequence fixed to the site.

23. The biochip reading method as claimed in claim 6, wherein a position of the site of the analysis based on the distribution of the light quantity of fluorescence generated at the site on the biochip corresponds to the position of the site on the biochip detected by the detection member based on the reflected light or the transmitted light of the illumination light.

24. The biochip reading method as claimed in claim 6, further comprising:
  illuminating the site by the transmitted light through the biochip.

25. The biochip reading method as claimed in claim 6, further comprising:
  fixing a biopolymer probe to the site; and
  binding a complementary base sequence to a DNA probe having the known base sequence which is fixed to the site.

26. The biochip reading method as claimed in claim 7, wherein a position of the site of the analysis based on the distribution of the light quantity of fluorescence generated at the site on the biochip corresponds to the position of the site on the biochip detected by the detection member based on the reflected light or the transmitted light of the illumination light.

27. The biochip reading method as claimed in claim 7, further comprising:
  illuminating the site by the transmitted light through the biochip.

28. The biochip reading method as claimed in claim 7, further comprising:
  fixing a biopolymer probe to the site; and
  binding a complementary base sequence to a DNA probe having the known base sequence which is fixed to the site.

* * * * *